(12) United States Patent
Natan et al.

(10) Patent No.: US 7,723,100 B2
(45) Date of Patent: May 25, 2010

(54) POLYMER COATED SERS NANOTAG

(75) Inventors: Michael J. Natan, Los Altos, CA (US); Remy Cromer, San Jose, CA (US); William E. Doering, Mountain View, CA (US); Ian D. Walton, Redwood City, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 408 days.

(21) Appl. No.: 11/622,915

(22) Filed: Jan. 12, 2007

(65) Prior Publication Data

US 2007/0165219 A1 Jul. 19, 2007

Related U.S. Application Data

(60) Provisional application No. 60/758,873, filed on Jan. 13, 2006.

(51) Int. Cl.
*C12M 1/34* (2006.01)
(52) U.S. Cl. .................................................. 435/287.1
(58) Field of Classification Search ....................... None
See application file for complete search history.

(56) References Cited

U.S. PATENT DOCUMENTS

| | | |
|---|---|---|
| 3,975,084 A | 8/1976 | Block |
| 4,039,297 A | 8/1977 | Takenaka |
| 4,313,734 A | 2/1982 | Leuvering |
| 4,802,761 A | 2/1989 | Bowen et al. |
| 4,853,335 A | 8/1989 | Olsen et al. |
| 4,920,059 A | 4/1990 | Moeremans et al. |
| 5,023,139 A | 6/1991 | Birnboim et al. |
| 5,059,394 A | 10/1991 | Phillips et al. |
| 5,096,809 A | 3/1992 | Chen et al. |
| 5,112,127 A | 5/1992 | Carrabba et al. |
| 5,137,827 A | 8/1992 | Mroczkowski et al. |
| 5,255,067 A | 10/1993 | Carrabba et al. |
| 5,266,498 A | 11/1993 | Tarcha et al. |
| 5,384,265 A | 1/1995 | Kidwell et al. |
| 5,441,894 A | 8/1995 | Coleman et al. |
| 5,445,972 A | 8/1995 | Tarcha et al. |
| 5,552,086 A | 9/1996 | Siiman et al. |
| 5,567,628 A | 10/1996 | Tarcha et al. |
| 5,580,492 A | 12/1996 | Bonnemann et al. |
| 5,609,907 A | 3/1997 | Natan |
| 5,637,508 A | 6/1997 | Kidwell et al. |
| 5,674,699 A | 10/1997 | Saunders et al. |
| 5,828,450 A | 10/1998 | Dou et al. |
| 5,825,790 A | 11/1998 | Lawandy |
| 5,833,924 A | 11/1998 | McClintock et al. |
| 5,864,397 A | 1/1999 | Vo-Dinh |
| 5,891,738 A | 4/1999 | Soini et al. |
| 5,935,755 A | 8/1999 | Kazmaier et al. |
| 5,958,704 A | 9/1999 | Starzl et al. |
| 6,020,207 A | 2/2000 | Liu |
| 6,027,890 A | 2/2000 | Ness et al. |
| 6,103,868 A | 8/2000 | Heath et al. |
| 6,136,610 A | 10/2000 | Polito et al. |
| 6,149,868 A | 11/2000 | Natan et al. |
| 6,200,820 B1 | 3/2001 | Hansen et al. |
| 6,219,137 B1 | 4/2001 | Vo-Dinh |
| 6,235,241 B1 | 5/2001 | Catt et al. |
| 6,274,323 B1 | 8/2001 | Bruchez et al. |
| 6,344,272 B1 | 2/2002 | Oldenburg et al. |
| 6,361,944 B1 | 3/2002 | Mirkin et al. |
| 6,422,998 B1 | 7/2002 | Vo-Dinh et al. |
| 6,436,651 B1 | 8/2002 | Everhart et al. |
| 6,451,619 B1 | 9/2002 | Catt et al. |
| 6,500,622 B2 | 12/2002 | Bruchez, Jr. et al. |
| 6,514,767 B1 | 2/2003 | Natan |
| 6,514,770 B1 | 2/2003 | Sorin |
| 6,558,956 B1 | 5/2003 | Carron et al. |
| 6,562,403 B2 | 5/2003 | Klabunde et al. |
| 6,587,197 B1 | 7/2003 | Rahbar-Dehghan |
| 6,595,427 B1 | 7/2003 | Soni et al. |
| 6,603,537 B1 | 8/2003 | Dietz et al. |
| 6,610,351 B2 | 8/2003 | Shchegolikhin et al. |
| 6,630,307 B2 | 10/2003 | Bruchez et al. |
| 6,642,012 B1 | 11/2003 | Ashdown |
| 6,646,738 B2 | 11/2003 | Roe |
| 6,649,138 B2 | 11/2003 | Adams et al. |
| 6,653,080 B2 | 11/2003 | Bruchez et al. |
| 6,682,596 B2 | 1/2004 | Zehnder et al. |
| 6,687,395 B1 | 2/2004 | Dietz et al. |
| 6,699,724 B1 | 3/2004 | West et al. |
| 6,730,400 B1 | 5/2004 | Komatsu et al. |

(Continued)

FOREIGN PATENT DOCUMENTS

EP 0 653 625 5/1995

(Continued)

OTHER PUBLICATIONS

Akerman, et al. (2002) "Nanocrystal targeting in vivo" PNAS, 99(20):12621.

(Continued)

*Primary Examiner*—Manjunath N Rao
*Assistant Examiner*—Bin Shen

(57) ABSTRACT

An encapsulated surface enhanced Raman scattering (SERS) tag. The tag includes a metal core and an encapsulant, typically a glass encapsulant. The encapsulant is further derivatized with a polymer.

7 Claims, 1 Drawing Sheet

U.S. PATENT DOCUMENTS

| | | | |
|---|---|---|---|
| 6,743,581 | B1 | 6/2004 | Vo-Dinh |
| 6,750,016 | B2 | 6/2004 | Mirkin et al. |
| 6,750,031 | B1 | 6/2004 | Ligler et al. |
| 6,759,235 | B2 | 7/2004 | Empedocles et al. |
| 6,778,316 | B2 | 8/2004 | Halas et al. |
| 6,815,064 | B2 | 11/2004 | Treadway et al. |
| 6,815,212 | B2 | 11/2004 | Ness et al. |
| 6,838,243 | B2 | 1/2005 | Lai et al. |
| 6,861,263 | B2 | 3/2005 | Natan |
| 6,919,009 | B2 | 7/2005 | Stonas et al. |
| 6,970,246 | B2 | 11/2005 | Hansen |
| 6,972,173 | B2 | 12/2005 | Su et al. |
| 7,045,049 | B1 | 5/2006 | Natan et al. |
| 7,079,241 | B2 | 7/2006 | Empedocles et al. |
| 7,098,041 | B2 | 8/2006 | Kaylor et al. |
| 7,102,747 | B2 | 9/2006 | Wang et al. |
| 7,102,752 | B2 | 9/2006 | Kaylor et al. |
| 7,105,310 | B1 | 9/2006 | Gray et al. |
| 7,122,384 | B2 | 10/2006 | Prober et al. |
| 7,123,359 | B2 | 10/2006 | Armstrong et al. |
| 7,141,212 | B2 | 11/2006 | Catt et al. |
| 7,192,778 | B2 | 3/2007 | Natan |
| 7,443,489 | B2 | 10/2008 | Natan |
| 2002/0142480 | A1 | 10/2002 | Natan |
| 2003/0232388 | A1 | 12/2003 | Kreimer et al. |
| 2005/0036148 | A1 | 2/2005 | Phelan |
| 2005/0037510 | A1 | 2/2005 | Sharrock et al. |
| 2005/0037511 | A1 | 2/2005 | Sharrock |

FOREIGN PATENT DOCUMENTS

| | | |
|---|---|---|
| EP | 0 703 454 | 3/1996 |
| EP | 1 181 091 | 2/2002 |
| WO | WO 88/07680 | 10/1988 |
| WO | WO 92/17781 | 10/1992 |
| WO | WO 98/04740 | 2/1998 |
| WO | WO 98/10289 | 3/1998 |
| WO | WO 99/21934 | 5/1999 |
| WO | WO 00/11024 | 3/2000 |
| WO | WO 00/27645 | 5/2000 |
| WO | WO 01/08081 | 2/2001 |
| WO | WO 01/25002 | 4/2001 |
| WO | WO 01/25510 | 4/2001 |
| WO | WO 01/25758 | 4/2001 |
| WO | WO 02/29136 | 4/2002 |
| WO | WO 02/068932 | 6/2002 |
| WO | WO 02/079764 | 10/2002 |
| WO | WO 03/021231 | 3/2003 |
| WO | WO 03/021853 | 3/2003 |
| WO | WO 2006/036130 | 4/2006 |
| WO | WO 2006/042111 | 4/2006 |
| WO | WO 2006/105110 | 10/2006 |

OTHER PUBLICATIONS

Ballou, et al. (2004) "Noninvasive imaging of quantum dots in mice" Bioconjugate Chem., 15(1):79-86.

Gao, et al. (2004) "In vivo cancer targeting and imaging with semiconductor quantum dots" Nature Biotechnology, 22(8): 969-76.

U.S. Appl. No. 09/598,395, filed Jun. 20, 2000, Natan et al.

U.S. Appl. No. 09/676,890, filed Jun. 20, 2000, Natan et al.

U.S. Appl. No. 09/677,198, filed Oct. 2, 2000, Natan et al.

Akbarian F. et al., "Porous Sol-Gel Silicates Containing Gold Particles as Matrices for Surface-Enhanced Raman Spectroscopy", Journal of Raman Spectroscopy; vol. 27, Issue 10, Oct. 1996, pp. 775-783.

Ascencio et al, " A truncated icosahedral structure observed in gold nanoparticles", Jorge A. Ascencio, Mario Surface Science, vol. 447, Issues 1-3, Feb. 20, 2000, pp. 73-80.

Averitt et al., "A metal nanoshell consists of a nanometer-scale dielectric core surrounded by a thin metallic shell. The plasmon resonance of metal nanoshells displays a geometric tunability", Josa B, vol. 16, Issue 10, 1999, pp. 1824-1832.

Brazdil et al., "Resonance Raman spectra of adsorbed species at solid-gas interfaces. Nitrosodimethylaniline adsorbed on silica and alumina surfaces", J. Phys. Chem., 1981, 85 (8), pp. 995-1004.

Bruchez et al., "Semiconductor nanocrystals as fluorescent biological labels", Science, Sep. 25, 1998, 281(5385), pp. 2013-2016.

Byahut et al., "Direct comparison of the chemical properties of single crystal Ag(111) and electrochemically roughened Ag as substrates for surface Raman scattering", Langmuir, 1991, 7 (3), pp. 508-513.

Chan et al., "Quantum dot bioconjugates for ultrasensitive nonisotopic detection", Science, 1998, 281, pp. 2016-2018.

U.S. Appl. No. 11/051,222, filed on Feb. 4, 2005.

U.S. Appl. No. 11/113,601, filed on Apr. 25, 2005.

U.S. Appl. No. 11/132,510, filed on May 18, 2005.

U.S. Appl. No. 11/132,974, filed on May 18, 2005.

U.S. Appl. No. 11/133,926, filed on May 20, 2005.

U.S. Appl. No. 11/134,129, filed on May 20, 2005.

U.S. Appl. No. 11/134,145, filed on May 20, 2005.

U.S. Appl. No. 11/611,052, filed on Dec. 14, 2006.

U.S. Appl. No. 12/245,538, filed on Oct. 3, 2008.

Co-Pending Appl. No. 12/245,555, filed on Oct. 3, 2008.

Dhere et al., "Twinned colloidal gold particles", Ultramicroscopy, vol. 18, Issues 1-4, 1985, pp. 415-417.

Duff et al., "The Morphology and Microstructure of Colloidal Silver and Gold Angewandte Chemie", International Edition in English, vol. 26, Issue 7, 1987, pp. 676-678.

El-Kouedi et al., "Optical Properties of Gold-Silver Nanoparticle Pair Structures", J. Phys. Chem. B, 104, 2000, pp. 4031-4037.

Emory et al., "Direct Observation of Size-Dependent Optical Enhancement in Single Metal Nanoparticles", Journal of the American Chemical Society, 1998, 120 (31), 8009-8010.

Emory et al., "Near-Field Surface-Enhanced Raman Spectroscopy on Single Silver Nanoparticles", Analytical Chemistry, 1997, 69 (14), pp. 2631-2635.

Emory et al., "Screening and Enrichment of Metal Nanoparticles with Novel Optical Properties", J. Phys. Chem. B, 1998, 102 (3), pp. 493-497.

European Patent Office, EP Supplementary Search Report prepared Apr. 18, 2008, for European Patent Application No. EP 05 85 6641, 4 pages.

Félidj et al., "A new approach to determine nanoparticle shape and size distributions of SERS-active gold-silver mixed colloids", New J. Chem., 1998, 22, pp. 725-732.

Freeman et al., "Ag-Clad Au Nanoparticles: Novel Aggregation, Optical, and Surface-Enhanced", Raman Scattering Properties, M.J, J. Phys. Chem., vol. 100, No. 2, 1996, pp. 718-724.

Grabar et al., "Preparation and Characterization of Au Colloid Monolayers", Analytical Chemistry, 1995, 67 (4), pp. 735-743.

Hall et al., "Cocondensation of Organosilica Hybrid Shells on Nanoparticle Templates: A Direct Synthetic Route to Functionalized Core-Shell Colloids", Langmuir, 2000, 16 (3), pp. 1454-1456.

Hoadk et al., "Laser-Induced Inter-Diffusion in AuAg Core-Shell Nanoparticles", J. Phys. Chem. B, 2000, vol. 104, pp. 11708-11718.

Horkans et al., "Pulsed Potentiostatic Deposition of Gold from Solutions of the Au(I) Sulfite Complex", Electrochem. Soc., 124, 1977, p. 1499.

Hua-Zhong Yu et al., "Surface-Enhanced Raman Scattering (SERS) from Azobenzene Self-Assembled Sandwiches", Langmuir, vol. 15, No. 1, 1999, pp. 16-19.

Jin et al., "Photoinduced Conversion of Silver Nanospheres to Nanoprisms", Science, Nov. 30, 2001, 294, pp. 1901-1903.

Keating et al., "Heightened Electromagnetic Fields Between Metal Nanoparticles: Surface Enhanced Raman Scattering from Metal-Cytochrome c-Metal Sandwiches", J. Phys. Chem. B, vol. 102, No. 47, 1998, pp. 9414-9425.

Keating et al., "Protein: Colloid Conjugates for Surface Enhanced Raman Scattering: Stability and Control of Protein Orientation", J. Phys. Chem. B, vol. 102, No. 47, 1998, pp. 9404-9413.

Kneipp et al., "Approach to Single Molecule Detection Using Surface-Enhanced Resonance Raman Scattering (SERRS): A Study Using Rhodamine 6G on Colloidal Silver", Applied Spectroscopy, vol. 49, Issue 6, pp. 12A-20A and 691-860, Jun. 1995, pp. 780-784.

Kneipp et al., "Detection and identification of a single DNA base molecule using surface-enhanced Raman scattering (SERS)", Rev. E 57, 1998, pp. R6281-R6284.

Kneipp et al., "Extremely Large Enhancement Factors in Surface-Enhanced Raman Scattering for Molecules on Colloidal Gold Clusters", Applied Spectroscopy, vol. 52, Issue 12, pp. 443A-455A and 1493-1626, Dec. 1998, pp. 1493-1497.

Kneipp et al., "Population Pumping of Excited Vibrational States by Spontaneous Surface-Enhanced Raman Scattering", Phys. Rev. Lett. 76, 1996, pp. 2444-2447.

Kneipp et al., "Single Molecule Detection Using Surface-Enhanced Raman Scattering (SERS)", Phys. Rev. Lett. 78, 1997, pp. 1667-1670.

Kneipp et al., "Single-Molecule Detection of a Cyanine Dye in Silver Colloidal Solution Using Near-Infrared Surface-Enhanced Raman Scattering", Applied Spectroscopy, vol. 52, Issue 2, pp. 72A-73A and 175-321, Feb. 1998, pp. 175-178.

Kneipp et al., "Surface-enhanced Raman scattering: A new tool for biomedical spectroscopy", Current Science, vol. 77, No. 7, Oct. 1999, pp. 915-926.

Kneipp et al., "Ultrasensitive Chemical Analysis by Raman Spectroscopy", Chem. Rev., 1999, 99 (10), pp. 2957-2976.

Kneipp, K., "High-sensitive Sers on colloidal silver particles in aqueous solution", Journal: Experimentelle Technik der Physik; vol. 36, No. 2, 1998, pp. 161-166.

Kovtyukhova et al., "Layer-by-Layer Assembly of Rectifying Junctions in and on Metal Nanowires", J. Phys. Chem. B, 2001, 105 (37), pp. 8762-8769.

Liz-Marzan et al., "Synthesis of Nanosized Gold-Silica Core-Shell Particles", Langmuir, 1996, 12 (18), pp. 4329-4335.

Lyon et al., "Confinement and Detection of Single Molecules in Submicrometer Channels", Analytical Chemistry, 1997, 69 (16), pp. 3400-3405.

Michaels et al., "Ag Nanocrystal Junctions as the Site for Surface-Enhanced Raman Scattering of Single Rhodamine 6G Molecules", J. Phys. Chem. B, 2000, 104 (50), pp. 11965-11971.

Michaels et al., "Surface Enhanced Raman Spectroscopy of Individual Rhodamine 6G Molecules on Large Ag Nanocrystals", J. Am. Chem. Soc., 1999, 121 (43), pp. 9932-9939.

Moskovits et al., "Sers and the Single Molecule: Near Field Microscopy and Spectroscopy", Spie, 2001, vol. 4258, pp. 43-49.

Mucic et al., "Dna-Directed Synthesis of Binary Nanoparticle Network Materials", J. Am. Chem. Soc., 120 (48), 1998, pp. 12674-12675.

Nicewarner Sr. et al., "Synthesis and characterization of well-defined metal nanoparticle-protein-metal nanoparticle sandwiches", Penn State University/University Pk//Pa/16802, Abstracts of Papers of The American Chemical Society, Aug. 23. 1998, vol. 216, 1, pp. 172-COLL.

Nicewarner-Peña et al., "Submicrometer Metallic Barcodes", Science, Oct. 5, 2001, 294, pp. 137-141.

Nie et al., " Probing Single Molecules and Single Nanoparticles by Surface-Enhanced Raman Scattering", Emory, Science, Feb. 21, 1997, vol. 275, No. 5303, pp. 1102-1106.

Nie, S., "Optical detection of single molecules; Annual Review of Biophysics and Biomolecular Structure", vol. 26, 1997, pp. 567-596.

Nikoobakht et al., "Preparation and Growth Mechanism of Gold Nanorods (NRs) Using Seed-Mediated Growth Method", Chem. Mater., 15, 2003, pp. 1957-1962.

Ron et al., "Self-Assembled Monolayers on Oxidized Metals. 2. Gold Surface Oxidative Pretreatment, Monolayer Properties, and Depression Formation", Langmuir, 14 (5), 1998, pp. 1116-1121.

Sandrock et al., "Synthesis and Second-Harmonic Generation Studies of Noncentrosymmetric Gold Nanostructures", J. Phys. Chem. B, 103, 1999, pp. 2668-2673.

Sandrock, "Synthesis and Linear Optical Properties of Nanoscopic Gold Particle Pair Structures", J. Phys. Chem. B, 103, 1999, pp. 11398-11406.

Shibata et al., "Preparation of Silica Microspheres Containing Ag Nanoparticles", Journal of Sol-Gel Science and Technology, vol. 11, No. 3, Aug. 1998, pp. 279-287.

Stöber et al., "Controlled growth of monodisperse silica spheres in the micron size range", Journal of Colloid and Interface Science, vol. 26, Issue 1, Jan. 1968, pp. 62-69.

Sun et al., "Fabrication of nanoporous single crystal mica templates for electrochemical deposition of nanowire arrays", Journal of Materials Science, vol. 35, No. 5, Mar. 2000, pp. 1097-1103.

Switzer et al., "Electrochemical Self-Assembly of Copper/Cuprous Oxide Layered Nanostructures", J. Am. Chem. Soc., 1998, 120 (14), pp. 3530-3531.

Ung et al., "Controlled Method for Silica Coating of Silver Colloids. Influence of Coating on the Rate of Chemical Reactions", Langmuir, 1998, 14 (14), pp. 3740-3748.

Van Duyne et al., "Atomic force microscopy and surface-enhanced Raman spectroscopy. I. Ag island films and Ag film over polymer nanosphere surfaces supported on glass", Chem. Phys., vol. 99, Issue 3, pp. 2101-2115.

Vo-Dinh, T., "Surface-enhanced Raman Spectroscopy using metallic nanostructures", Trends in Analytical Chemistry, vol. 17, No. 8-9, 1998, XP002314222.

Walton et al., "Particles for Multiplexed Analysis in Solution: Detection and Identification of Striped Metallic Particles Using Optical Microscopy", Analytical Chemistry, 74 (10), 2002, pp. 2240-2247.

Wasileski et al., "Surface-Enhanced Raman Scattering from Substrates with Conducting or Insulator Overlayers: Electromagnetic Model Predictions and Comparisons with Experiment", Applied Spectroscopy, 2000, vol. 54, pp. 761-772.

POLYMER COATED SERS NANOTAG

RELATED APPLICATION

This application claims priority from U.S. Provisional Application Ser. No. 60/758,873, filed on Jan. 13, 2006, entitled "Polymer Coated SERS Nanotag", the contents of which are incorporated herein in their entirety.

TECHNICAL FIELD

The present invention is directed toward a SERS nanotag and more particularly toward a SERS nanotag having a polymer coating.

BACKGROUND OF THE INVENTION

SERS nanotags are glass coated metal nanoparticles that produce a strong Raman scattering signal when excited by visible and near infrared light. SERS nanotags may be used to perform in vivo assays. Native nanotags, however, appear to the body as foreign objects and so will usually be cleared by the body quickly.

The present invention is directed toward overcoming one or more of the problems discussed above.

DETAILED DESCRIPTION

I. Introduction

Figure 1:
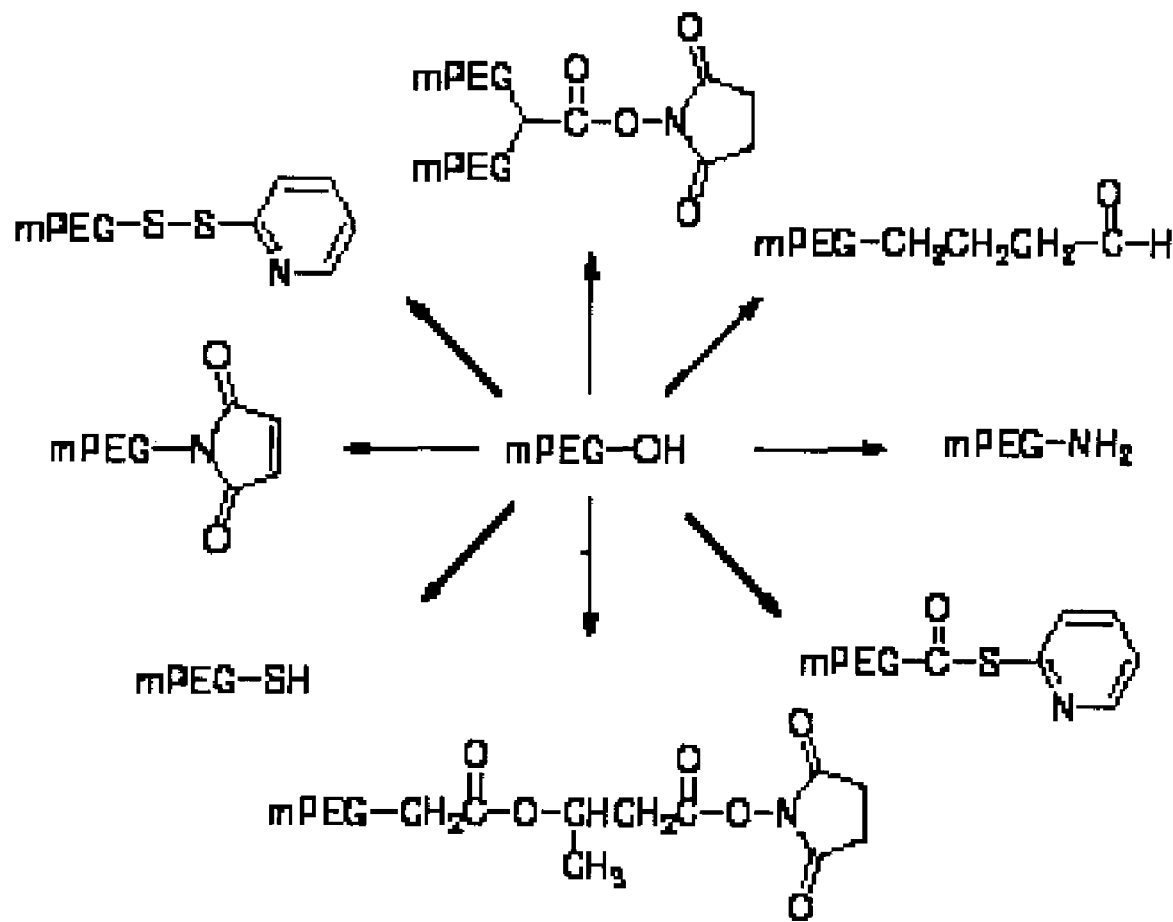
FIG. 1 is a reagent chart concerning PEGylation.

SERS nanotags are glass coated metal nanoparticles that produce a strong Raman scattering signature when excited by visible and near infrared light. They may be used to perform In-Vivo assays where specific physiological regions, cells, tumour, tissues etc. are targeted by the SERS nanotags as a diagnostic label similar to a fluorophore. Native particles will appear to the body as foreign bodies and so will usually be cleared by the body quickly. Coating in vivo diagnostic particles in polymers can reduce the rate at which particles are cleared by the body.

SERS nanotags are glass coated and so can be subsequently coated by a variety of different molecules, using a variety of different attachment methods. Polymers are coated on particles to increase their retention time the body. Typical polymers used are PEGS (polyethylene glycol), Dextrans etc. PEGS used typically need to be greater than 5000 Da. Particles can be further modified by attaching proteins or antibodies specific for selected physiological regions. Indeed the flexibility of glass attachment chemistry means that a combination of polymers and proteins can be employed which will allow the user to optimize site specificity and retention time. Other particles, e.g Quantum Dots, cannot be as easily coated with a variety of polymers. Therefore the SERS nanotags ability to be retained by the circulation system should be greater than that of Quantum Dots and other particles.

REFERENCES

Gao et al. (Jul. 18, 2004) Nature Biotechnology "In vivo cancer targeting and imaging with semiconductor quantum dots."
Åkerman et al. (2002) PNAS 99(20):12621 "Nanocrystal targeting in vivo."
Ballou et al. (2004) Bioconjugate Chem. 15:79-86.

II. SERS Nanotags

One embodiment of the present invention includes the use of encapsulated surface enhanced Raman scattering (SERS) tags. These nanoparticles, referred to as SERS nanotags, include a metal nanoparticle, which metal is Raman enhancing; a Raman-active molecule (sometimes referred to as a SERS tag or reporter molecule) attached to, or associated with the surface of the nanoparticle; and an encapsulant, usually $SiO_2$ (glass). The encapsulant surrounds both the metal nanoparticle and the Raman-active molecule. A particle prepared in this fashion has a measurable SERS spectrum. Although the invention is described in terms of SERS nanotags prepared from single nanoparticles, it is to be understood that nanoparticle core clusters or aggregates may be used in the preparation of SERS nanotags. Methods for the preparation of clusters of aggregates of metal colloids are known to those skilled in the art. The use of sandwich-type particles is described in U.S. Pat. No. 6,861,263, which patent is incorporated herein by reference.

SERS data may be obtained from the tags by illuminating the SERS nanotags with a suitable excitation wavelength. In the case of some reporter molecules excitation wavelengths are in the range of about 600-1000 nm. In some embodiments, the excitation wavelengths are 632.8, 785, or 980 nm. Examples of reporter molecules include 4-mercaptopyridine (4-MP); trans-4,4' bis(pyridyl)ethylene (BPE); quinolinethiol; 4,4'-dipyridyl, 1,4-phenyldiisocyanide; mercaptobenzamidazole; 4-cyanopyridine; 1',3,3,3',3'-hexamethylindotricarbocyanine iodide; 3,3'-diethyltiatricarbocyanine; malachite green isothiocyanate; bis-(pyridyl)acetylenes; Bodipy, and isotopes thereof, including, for example, deuterated BPE, deuterated 4,4'-dipyridyl, and deuterated bis-(pyridyl)acetylenes; as well as pyridine, pyridine-d5 (deuterated pyridine), and pyridine-$^{15}$N. A suitable excitation wavelength is one at which the background noise component, generated by fluorescence from other fuel components is low enough to obtain a detectable SERS signal.

The SERS nanotags may comprise any nanoparticle core known in the art to be Raman-enhancing. As used herein, the term "nanoparticle", "nanostructure", "nanocrystal", "nanotag," and "nanocomponent" are used interchangeably to refer to a particle, generally a metallic particle, having one dimension in the range of about 1 nm to about 1000 nm. In some embodiments, the metal nanoparticle core is a spherical or nearly spherical particle of 20-200 nm in diameter. In some embodiments the range is about 20 nm to about 50 nm, in some embodiments in the range of about 30 nm to about 100 nm. The tags may be polydisperse. That is, a group of tags may comprise tags with these ranges of diameters, but each tag need not have the same diameter.

Nanoparticles may be isotropic or anisotropic. Anisotropic nanoparticles may have a length and a width. In some embodiments, the length of an anisotropic nanoparticle is the dimension parallel to the aperture in which the nanoparticle was produced. In the case of anisotropic nanoparticles, in some embodiments, the nanoparticle has a diameter (width) of 350 nm or less. In other embodiments, the nanoparticle has a diameter of 250 nm or less and in some embodiments, a diameter of 100 nm or less. In some embodiments, the width is between 15 nm to 300 nm. In some embodiments, the nanoparticle has a length of about 10-350 nm.

Nanoparticles include colloidal metal, hollow or filled nanobars, magnetic, paramagnetic, conductive or insulating nanoparticles, synthetic particles, hydrogels (colloids or bars), and the like. The nanoparticles used in the present invention can exist as single nanoparticles, or as clusters or aggregates of the nanoparticles. Clusters or aggregates may be formed by the addition of aggregating agents to the SERS nanotags.

It will also be appreciated by one of ordinary skill in the art that nanoparticles can exist in a variety of shapes, including but not limited to spheroids, rods, disks, pyramids, cubes, cylinders, nanohelixes, nanosprings, nanorings, rod-shaped nanoparticles, arrow-shaped nanoparticles, teardrop-shaped nanoparticles, tetrapod-shaped nanoparticles, prism-shaped nanoparticles, and a plurality of other geometric and non-geometric shapes. Another class of nanoparticles that has been described include those with internal surface area. These include hollow particles and porous or semi-porous particles. Moreover, it is understood that methods to prepare particles of these shapes, and in certain cases to prepare SERS-active particles of these shapes, have been described in the literature. While it is recognized that particle shape and aspect ratio can affect the physical, optical, and electronic characteristics of nanoparticles, the specific shape, aspect ratio, or presence/absence of internal surface area does not bear on the qualification of a particle as a nanoparticle.

Various systems can be used for detection of SERS nanotags. A number of commercially available instruments may be used. For example, Raman Systems Inc., Enwave Optronics, Inc., Kaiser Optical Systems, Inc., InPhotonics, Inc., J-Y Horiba, Renishaw, Bruker Optics, Thermo Electron, Avalon, GE Ion Track, Delta Nu, Concurrent Analytical, Raman Systems, Inphotonics, ChemImage, Jasco, Lambda Systems, SpectraCode, Savante, Real-Time Analyzers, Veeco, Witec, and other companies provide Raman spectrometers suitable for use in the present invention.

III. Polymer Coated SERS Nanotags

The glass coated SERS nanotags described above can be derivatized with polymers using a variety of methods.

The native glass coat serves at least 2 purposes:

Sequester and stabilize the Raman active Tag by encapsulation of the adsorbed tag on the metallic surface.

Provide a surface that can be easily modified with a variety of well known attachment chemistries leading to versatile and functional surfaces.

These surfaces are amenable to the development of robust and controllable methods for bioconjugation. Indeed, the surface silanol groups can be easily derivatized with commercially available mercapto-, carboxy-, amino-, aldehydo- and epoxy-silane reagents.

The introduction of the functional groups has been done by 2 alternate routes:

Direct derivatization with functional silanes. Only functional silane reagent is reacted directly with glass-coated NBC. This approach was also used for Glass vial derivatization.

Derivatization in presence of TEOS. These is a 2-glass layer approach whereby the functional silane is introduced along with a second TEOS treatment.

These functionalization routes provide the flexibility to conjugate practically any type of molecule. This method takes advantage of the large library of functional PEGs provided by Nektar (form. Shearwater) to generate many PEGylated tags. (See FIG. 1 taken from Nektar website www.nektar.com).

PEG may thus provide biocompatibility and extended in-vivo lifetimes of the SERS tags.

To achieve a similar extended bioavailability the tags can alternatively be coated with other molecules such as with proteins, DNA, RNA, synthetic Polyaminoacids (Polylysine, Polyglutamic acid), Polyethylene glycols, block copolymer dendrimers, polyamides, polyethylenimines, polyacrylates and other natural polymers such as Dextrans and other natural carbohydrate based polymers

EXAMPLES

The following examples are provided for illustrative purposes only and are not intended to limit the scope of the invention.

Functionalization of Glass coated SERS tags using the 2 Glass-layer approach:

Materials & Reagents

APTMS; Aminopropyltrimethoxysilane was purchased from Aldrich

MPTMS Mercaptopropyltrimethoxysilane was purchased from Fluka

CEST Carboxyethylsilane triol was purchased from Gelest

GPTMS: 3-Glycidoxypropyl)-Trimethoxysilane was from United Chemical Technologies TEOS Tetraethylorthosilicate was purchased from Sigma $NH4OH$ 20×BPE M8.3 Glass coated SERS tags were prepared in-house by Frances Wong Amino-Tags: APTMS derivatization of Glass coated SERS tags 1. Take 15 ml conical Prolypropylene tube
2. Add 8 mL EtOH
3. Add 2 mL 20× tag
4. Add 0.5 mL NH4OH
5. Add 40 ul solution of 5% APTMS in TEOS
6. Mix on turning wheel for 60 nm at room Temp
7. Centrifuge 40 nm 35000 rpm
8. Wash 2 times with 10 ml DI water
9. Wash 2 times with 1.5 ml DI water
10. Store in 1000 ul water→concentration is 40×

Epoxy-Tags: GPTMS derivatization of Glass coated SERS tags

1. Take 15 ml conical Prolypropylene tube
2. Add 8 mL EtOH
3. Add 2 mL 20× tag
4. Add 0.5 mL NH4OH
5. Add 40 ul solution of 5% GPTMS in TEOS
6. Mix on turning wheel for 60 nm at room Temp
7. Centrifuge 40 nm 35000 rpm
8. Wash 2 times with 10 ml DI water
9. Wash 2 times with 1.5 ml DI water
10. Store in 1000 ul water→concentration is 40×

Thiolated-Tags: MPTMS derivatization of Glass coated SERS tags (this is the protocol for conventional tag preparation)

1. Take 15 ml conical Prolypropylene tube
2. Add 8 mL EtOH
3. Add 2 mL 20× tag
4. Add 0.5 mL NH4OH
5. Add 10 ul solution of 5% MPTMS in TEOS
6. Mix on turning wheel for 60 nm at room Temp
7. Centrifuge 40 nm 35000 rpm
8. Wash 2 times with 10 ml DI water
9. Wash 2 times with 1.5 ml DI water
10. Store in 1000 ul water→concentration is 40×

Carboxy-Tags: CEST derivatization of Glass coated SERS tags

11. Take 15 ml conical Prolypropylene tube
12. Add 8 mL EtOH
13. Add 2 mL 20× tag
14. Add 0.5 mL NH4OH
15. Add 40 ul solution of 5% CEST in TEOS 16. Mix on turning wheel for 60 nm at room Temp
17. Centrifuge 40 nm 35000 rpm
18. Wash 2 times with 10 ml DI water
19. Wash 2 times with 1.5 ml DI water
20. Store in 1000 ul water→concentration is 40×

General Direct derivatization method for functionalization of Glass coated SERS tags
1. Take 15 ml conical Prolypropylene tube
2. Add 8 mL EtOH
3. Add 2 mL 20× tag
4. Add solution of 2% silane/2% water in EtOH (1 ml)
5. Mix on turning wheel for 60 nm at room Temp
6. Centrifuge 40 nm 35000 rpm
7. Add 5 ml Ethanol and place on hot plate (50 C) for 30 nm
8. Wash 2 times with 10 ml DI water
9. Wash 2 times with 1.5 ml DI water
10. Store in 1000 ul water→concentration is 40×

Derivatization of Functional Glass-coated SERS Tags with PEG derivatives

Amino-Tag derivatization with mPEG-SPA, Fluorescein-PEG-NHS & Succinic Anhydride
Materials & Reagents
Amino-Tag (via APTMS)
Succinic Anhydride from Aldrich
mPEG-SPA was from Nektar
Fluorescein-PEG-NHS was from Nektar
PBS Amine derivatization with Succinic Anhydride
1. 300 ul (10×) RC121-2A Amino Tags
2. 300 ul Borate buffer
3. Dissolve 0.04 g succinic anhydride in 1 mL DMSO
4. Add 10 uL succinic anhydride solution to Amino Tags. Mix for 20 nm
5. Check pH.
6. Repeat #3 if necessary.
7. Incubate at RT for 2 hrs
8. Wash 2× with H2O using centrifugation
9. Store in 300 ul H2O Amine derivatization with mPEG-SPA
1. 300 ul (10×) Amino Tags
2. 300 ul PBS
3. Dissolve 0.01 g mPEG-SPA in 1 mL PBS
4. Add 100 uL solution to Amino Tags.
5. Incubate at RT for 2 hrs
6. Wash 2× with H2O using centrifugation
7. Store in 300 ul H2O Amine derivatization with Fluorescein-PEG-NHS
1. 300 ul (10×) Amino Tags
2. 300 ul PBS
3. Dissolve 0.01 g Fluorescein-PEG-NHS in 1 mL PBS
4. Add 100 uL solution to Amino Tags.
5. Incubate at RT for 2 hrs
6. Wash 2× with H2O using centrifugation
7. Store in 300 ul H2O Epoxy-Tag derivatization with mPEG-NH2 & NH2-PEG-Carboxylate
Materials & Reagents
Epoxy-Tag (via (3-Glycidoxypropyl)-Trimethoxysilane. United Chemical Technologies)
mPEG-NH2 was from Nektar
NH2-PEG-Carboxylate was from Nektar
Borate buffer Epoxide reaction with mPEG-NH2
1. 300 ul (10×) Epoxy-Tag
2. 300 ul Borate buffer
3. Dissolve 0.01 g mPEG-NH2 in 1 mL Borate buffer
4. Add 100 uL mPEG-NH2 solution to Epoxy-Tags
5. Incubate at RT for 60 nm
6. Wash 2× with H2O using centrifugation
7. Store in 300 ul H2O Epoxide Reaction with NH2-PEG-Carboxylate
1. 300 ul (10×) Epoxy-Tag
2. 300 ul Borate buffer
3. Dissolve 0.01 g NH2-PEG-Carboxylate in 1 mL Borate buffer.
4. Add 100 uL g NH2-PEG-Carboxylate solution to Epoxy-Tags
5. Incubate at RT for 60 nm
6. Wash 2× with H2O using centrifugation
7. Store in 300 ul H2O Thiolated-Tag derivatization with Maleimido-mPEGs
Materials & Reagents
Thiolated-Tag, 40× in Di water
mPEG-MAL-5,000 is from Nektar
mPEG-MAL-20,000 is from Nektar Thiol reaction with Maleimido-mPEG-5,000
1. Thiolated-Tag is resuspended in PBS w/o Calcium and Magnesium chloride at a concentration of 40× (1 mL)
2. Prepare mPEG-MAL-5000 at 10 mg/ml in the same buffer
3. Add 200 uL mPEG-MAL-5000 solution to Thiolated-Tags
4. Incubate at RT for 3 hrs
5. Wash 2× with 1 mL H2O using centrifugation
6. Wash 2× with 1 mL PBS w/o Calcium and Magnesium chloride using centrifugation
7. Wash 2× with 1 mL PBS with Calcium and Magnesium chloride using centrifugation
8. Store in 1 mL PBS with Calcium and Magnesium chloride at 40×

Thiol reaction with Maleimido-mPEG-20,000
1. Thiolated-Tag is resuspended in PBS w/o Calcium and Magnesium chloride at a concentration of 40× (1 mL)
2. Prepare mPEG-MAL-20,000 at 10 mg/ml in the same buffer
3. Add 200 uL mPEG-MAL-20,000 solution to Thiolated-Tags
4. Incubate at RT for 3 hrs
5. Wash 2× with 1 mL H2O using centrifugation
6. Wash 2× with 1 mL PBS w/o Calcium and Magnesium chloride using centrifugation
7. Wash 2× with 1 mL PBS with Calcium and Magnesium chloride using centrifugation
8. Store in 1 mL PBS with Calcium and Magnesium chloride at 40×

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims.

What is claimed is:

1. A coated nanotag comprising: a SERS-active nanotag; and a polymer coating completely covering the SERS active nanotag, wherein the SERS-active nanotag comprises: a core comprising one or more nanoparticles, a Raman-active molecule attached to or associated with the core, and an encapsulant.

2. The coated nanotag according to claim 1, wherein the core comprises a single nanoparticle.

3. The coated nanotag according to claim 1, wherein the core comprises a plurality of nanoparticles.

4. The coated nanotag according to claim 1, wherein the encapsulant comprises glass.

5. The coated nanotag according to claim 1, wherein the polymer comprises polyethylene glycol.

6. The coated nanotag according to claim 1, wherein the polymer comprises one or more polymers selected from the group consisting of polyethylene glycol, synthetic polyaminoacids, block copolymer dendrimers, polyamides, polyethylenimines, polyacrylates, and natural carbohydrates.

7. The coated nanotag according to claim 1, wherein the coated nanotag has a longer in vivo retention time as compared to an identical nanotag without the polymer coating.

* * * * *